United States Patent [19]

Udell et al.

[11] Patent Number: 4,785,821

[45] Date of Patent: Nov. 22, 1988

[54] PRESSURE MONITOR AND REGULATING DEVICE FOR ADMINISTRATION OF MEDICAMENT

[75] Inventors: Irving C. Udell, Northbrook; Arnold M. Schacter, Vernon Hills, both of Ill.

[73] Assignee: Ethitek Pharmaceuticals Co., Skokie, Ill.

[21] Appl. No.: 50,532

[22] Filed: May 15, 1987

[51] Int. Cl.⁴ ............................................. A61B 5/02
[52] U.S. Cl. .................................... 128/674; 128/748; 604/118
[58] Field of Search ................ 128/674, 748; 604/118, 604/246, 262

[56] References Cited

U.S. PATENT DOCUMENTS 3,690,312  9/1972  Leibinsohn ..................... 604/118 X
3,730,168  5/1973  McWhorter ..................... 128/674 X
4,170,224 10/1979  Garrett et al. ....................... 128/748

Primary Examiner—Dalton L. Truluck
Attorney, Agent, or Firm—Jones, Day, Reavis & Pogue

[57] ABSTRACT

A device for monitoring and limiting the fluid pressure during parenteral or intravenous administration of medication to a patient. The device includes a manometer tube connected at its lower end via a stopcock to the tubing through which the medication is administered under pressure, such as from a fluid pump. A graduated manometer bag is attached at the upper end of the manometer tube for receiving medication which overflows the manometer tube in the event excessive pressure is encountered as would happen if a blockage in the patient were to occur.

6 Claims, 1 Drawing Sheet

PRESSURE MONITOR AND REGULATING DEVICE FOR ADMINISTRATION OF MEDICAMENT

BACKGROUND OF THE INVENTION

This invention relates in general to a device for monitoring and regulating fluid pressure and, in particular, to a device for regulating and monitoring fluid pressure during administration of medicament to a patient.

Devices for simply monitoring fluid pressure (for example blood pressure) in a patient are known and used in the art. Typically, these devices consist of a graduated manometer tube in communication with fluid being administered to a patient from an I.V. bottle. A stopcock is provided to control the fluid flow between the I.V. bottle, manometer and patient. To continuously monitor the patient's venous pressure, the stopcock is set so that I.V. solution can flow to both the patient and the manometer. As the patient's blood pressure increases due to the addition of the I.V. solution, the increase is indicted by a rise in the fluid level in the manometer. Since the manometer is graduated, changes in the central venous pressure can be monitored.

These prior art devices, while adequate for monitoring venous pressure are not suitable for other uses as, for example, where medication is to be pumped into a patient and there is the possibility of blockage. Such devices are typically used in a closed system which does not provide an outlet for excess fluid should fluid pressure increase beyond a safe value. As a result, use of such devices for pressurized administration of medicament could result in rupture of blood vessels or other harm to the patient.

It is therefore an object of the present invention to provide a monitoring and regulating means to prevent an excessive increase in fluid pressure during pressurized administration of medicament.

A further object of the invention is to provide a means for capturing and measuring the overflow of fluid from the manometer to determine how much of the fluid was not administered to the patient.

A still further object of the invention is to provide a fluid administrative device which does not need to be continually monitored.

These and other objects and advantages will become apparent from the following description.

SUMMARY OF THE INVENTION

The invention relates to a fluid pressure monitor and regulator positioned between a patient and a fluid to be administered under pressure. The device comprises a graduated manometer tube connected at its lower end by means of a stopcock to the tubing through which fluid is administered to the patient and a graduated manometer bag attached at the upper end of the manometer tube for receiving overflow fluid. The manometer bag includes a drainage tube through which the excess fluid can be removed.

BRIEF DESCRIPTION OF THE DRAWINGS

The invention itself is set forth in the claims appended hereto and forming a part of the specification while an understanding of the embodiments thereof may be had by reference to the detailed description taken in conjunction with the drawing which is a front view of the pressure monitoring device of the invention.

DETAILED DESCRIPTION

Figure 1:
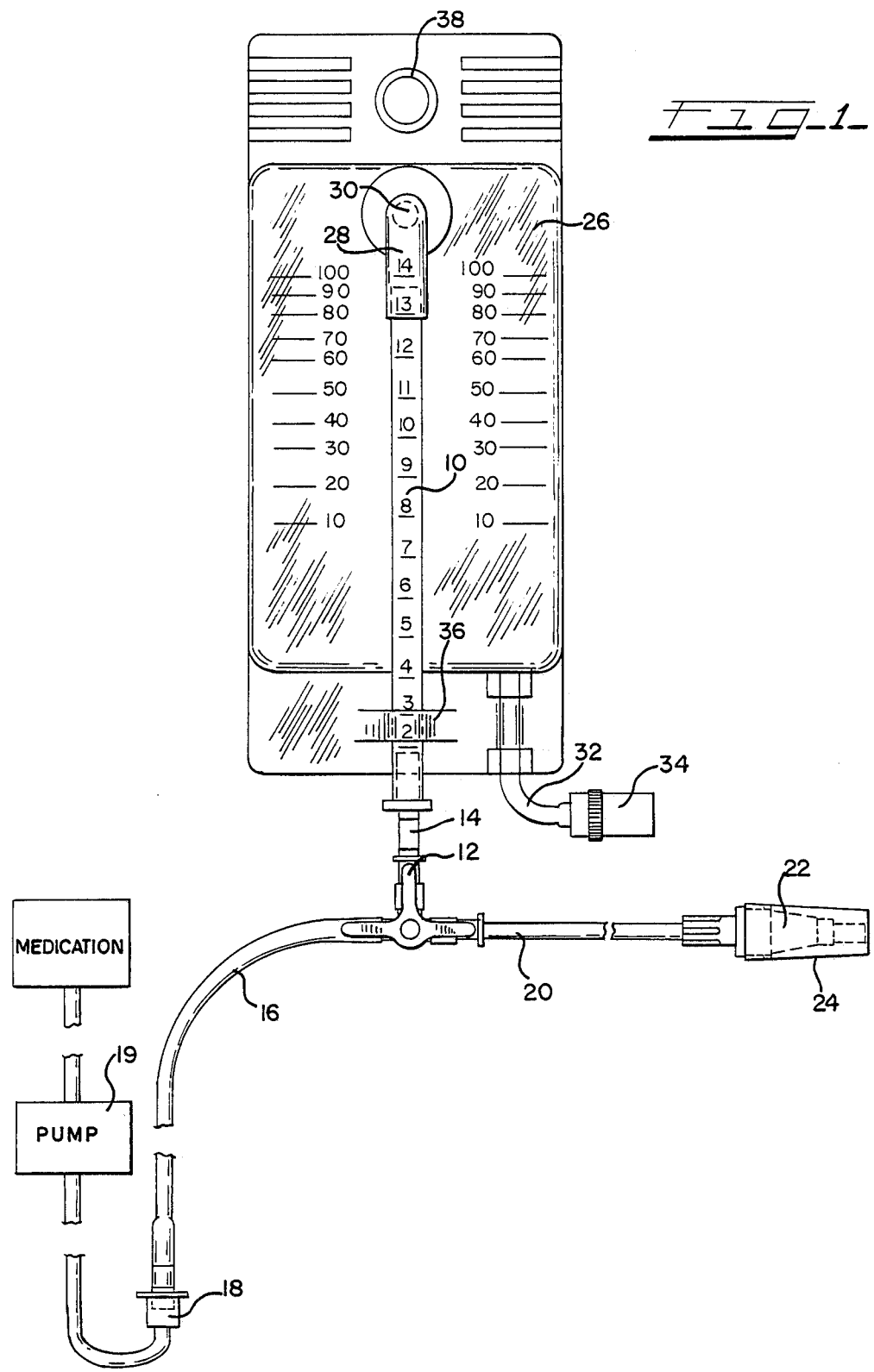

Referring to the drawing, a pressure monitoring device according to a preferred embodiment of the invention is illustrated. The device comprises a graduated manometer tube 10 connected at its lower end to a four-way stopcock 12 or similar valve device. Preferably, the manometer tube 10 is formed of a flexible plastic material and fits over a rigid plastic connector 14 which joins the manometer 10 to the stopcock 12.

Tubing 16 is secured, at one end to the stopcock 12, and at its other end to an adapted 18. A pump, shown generally in the Figure as 19, is attached to the adapter 18 and pumps fluid, such as medicament, into tubing 16. A second tube 20 is attached at one end to the stopcock 12, opposite tube 16, so that the tubing 16 and 20 form a continuous passage through the body of the stopcock 12 when the stopcock is in an open position, as shown in the Figure. The other end of tube 20 carries an adapter 22 which is attached to, for example, a parenteral of I.V. catheter (not shown) for administering medication parenterally or intravenously. Cap 24 covers adapter 22 until the device is ready for use.

A graduated manometer bag 26 communicates with the upper end of the manometer tube 10. Preferably, a small section of tubing 28, forming a right angle, is securely attached to the manometer bag 26 over an opening 30 in the bag. The upper end of the manometer tube 10 fits securely into the lower end of tubing 28 to form a continuous passage between tube 10, tubing 28 and the manometer bag 26. The continuous passage permits overflow fluid from manometer tube 10 to enter manometer bag 26 through opening 30. The lower end of the tube 10 fits through two slits in the manometer bag 26 which form a strip 36. The strip 36 rides over the tube 10 and keeps the manometer bag 26 anchored to the tube 10. The bag 26 may be provided with an opening 38 for attaching the system to an I.V. pole or ceiling hook.

The manometer bag 26 includes a drainage tube 32 through which fluid in the bag may be removed. A stopper 34 attached to the lower end of the drainage tube 32 and having a self-sealing silicon disk prevents fluid from leaking out of the drainage tube 32. When it is desired to remove the fluid in the bag 26, a hypodermic needle is inserted through the stopper 34 by puncturing the silicon disk and the fluid is aspirated out of the bag.

In operation, the adapter 18 is attached to the pump 19 for administering the medication and the a adapter 22 is attached to a catheter previously inserted in the patient. The stopcock 12 is adjusted to the open position so that the tubings 16 and 20 are in communication with each other and with the manometer tube 10. Medication is then pumped into the patient via tubings 16 and 20. As the fluid pressure in the patient rises due to the administration of the medication, the liquid level in the manometer tube 10 rises. The fluid pressure in the patient can be monitored by reading the calibrations on the manometer tube. If a blockage occurs in the patient, due for example to swelling of tissue, the fluid pressure in the patient will rise due to the action of the pump. If the fluid pressure rises above a safe value the regulating function of the invention comes into play. The blocked fluid rises in the manometer tube 10 and spills over into the manometer bag 26. Since the manometer bag is graduated, it is possible to determine the amount of medication that was not administered to the patient.

Thus, the manometer bag 26 regulates the pressure and provides an outlet for the overflow of medication until the blockage can be detected and corrected, preventing serious injury to a patient.

It will be understood that various changes and modifications can be made in the above-described embodiment of the invention without departing from the spirit thereof, particularly as defined by the following claims.

What is claimed is:

1. A device for monitoring and regulating the fluid pressure to a patient receiving a driven fluid through a catheter comprising:
   (a) a tube means for communicating the driven fluid from a supply to a patient;
   (b) a manometer in circuit with said tube means for indicating the fluid pressure therein;
   (c) overflow means comprising a manometer bag for limiting the fluid pressure to a selected value, said manometer bag communicating with said manometer to receive fluid when the fluid pressure exceeds said selected value.

2. A device according to claim 1 wherein said tube means communicates with said manometer through a valve means.

3. A device according to claim 2 wherein said valve means is a four-way stopcock.

4. A device according to claim 1 wherein the manometer bag includes a drainage tube for removing overflow fluid.

5. A device for monitoring and regulating the fluid pressure to a patient receiving a driven fluid through a catheter comprising:
   a manometer tube,
   a valve means attached to said manometer tube at its lower end,
   at least one tube for administering the fluid to the patient, said tube being attached to said valve means and communicating with said manometer tube when said valve means is in an open position, and
   a manometer bag attached to said manometer tube at its upper end and communicating therewith for limiting the fluid pressure to a selected value and capturing fluid which overflows from said manometer tube when the fluid pressure exceeds the selected value.

6. A device according to claim 5 wherein the valve means is a four-way stopcock.

* * * * *